United States Patent
Peter et al.

(10) Patent No.: US 7,115,874 B2
(45) Date of Patent: Oct. 3, 2006

(54) MISSION-SPECIFIC POSITRON EMISSION TOMOGRAPHY

(75) Inventors: William Peter, Bethesda, MD (US); Irving N. Weinberg, Bethesda, MD (US); Stephen T. Yarnall, Poway, CA (US)

(73) Assignee: Naviscan PET Systems, Inc., Rockville, MD (US)

( * ) Notice: Subject to any disclaimer, the term of this patent is extended or adjusted under 35 U.S.C. 154(b) by 285 days.

(21) Appl. No.: 10/637,490

(22) Filed: Aug. 11, 2003

(65) Prior Publication Data

US 2004/0026620 A1    Feb. 12, 2004

Related U.S. Application Data

(60) Provisional application No. 60/402,535, filed on Aug. 12, 2002.

(51) Int. Cl.
*G01T 1/164* (2006.01)

(52) U.S. Cl. .................................. 250/363.03
(58) Field of Classification Search ........... 250/363.03
See application file for complete search history.

(56) References Cited

U.S. PATENT DOCUMENTS

| | | | |
|---|---|---|---|
| 5,252,830 A | 10/1993 | Weinberg | |
| 5,287,273 A * | 2/1994 | Kupfer et al. | 600/431 |
| 5,636,299 A | 6/1997 | Bueno et al. | |
| 6,271,510 B1 | 8/2001 | Boxen | |
| 6,331,703 B1 | 12/2001 | Yarnall et al. | |
| 6,559,440 B1 | 5/2003 | Yarnall et al. | |
| 6,628,984 B1 * | 9/2003 | Weinberg | 600/436 |
| 6,674,083 B1 * | 1/2004 | Tanaka et al. | 250/363.03 |
| 6,852,980 B1 * | 2/2005 | Jones et al. | 250/369 |
| 2001/0040219 A1 | 11/2001 | Cherry et al. | |
| 2003/0036700 A1 | 2/2003 | Weinberg | |

FOREIGN PATENT DOCUMENTS

WO    WO 01/79884 A2    10/2001

OTHER PUBLICATIONS

Driscoll, J.R. et al., "Asymptotically Fast Algorithms for Spherical and Related Transforms" Annual Symposium on Foundations of Computer Science, 1989, pp. 344-349, Research Triangle Park, North Carolina.

(Continued)

*Primary Examiner*—David Porta
*Assistant Examiner*—Mindy Vu
(74) *Attorney, Agent, or Firm*—Katten Muchin Rosenman LLP (57) ABSTRACT

A handheld gamma camera or PET system with a disposable detector head is provided. This system includes a configuration of a gamma camera or PET scanner in which optical fibers or bundles of optical fibers are coupled to a scintillator or array of scintillators and the other end of the optical fibers or bundles of optical fibers are coupled to a light-sensitive camera, such as a photomultiplier. The system may further include a mechanism to rapidly couple and/or decouple the optical fiber or fibers from the light sensitive camera or from the scintillator or array of scintillators so that the detector can be disposed of or sterilized without damaging the light-sensitive camera. A method for image reconstruction and image simulation is also provided. The method includes an application of deterministic sampling using Gaussian quadrature parameters to construct a transition matrix for purposes of image reconstruction.

4 Claims, 5 Drawing Sheets

OTHER PUBLICATIONS

Leblanc, J.W. et al., "C-Sprint: A Prototype Compton Camera System for Low Energy Gamma Ray Imaging" Nuclear Science Symposium, 1997, pp. 357-361, Albuqueeque, New Mexico.

Maniatis, T.A., et al. "A Generalised Diffraction Tomography Technique Based on Non-Linear Optimization and Gaussian Basis Expansion of the Scatterer" Engineering in Medicine and Biology., 18th Annual International Conference of the IEEE Engineering in Medicine and Biology Society, 1996, pp. 724-725, Amsterdam, Netherlands.

S. Holbrook, "Newsline Commentary", Journal of Nuclear Medicine 43(2), Feb. 2002, pp. 11N-12N.

L.P. Adler et al., "Evaluation of Breast Masses and Axillary Lymph Nodes with [F-18] 2-Deoxy-2-fluoro-D-glucose PET", Radiology, Jun. 1993, vol. 187, No. 3: 743-750.

B. Fisher et al., "Cancer of the Breast: Size of Neoplasm and Diagnosis", Cancer, 1969, vol. 24, No. 5:1071-1080.

R.M. Kessler et al., "Analysis of emission tomographic scan data: limitations imposed by resolution and background", J. Comput. Assist Tomography, 1984, 8(3):514-522.

C. Chen, L. Adler et al., "Simultaneous Recovery of Size and Radioactivity Concentration of Small Spheroids with PET Data", J. Nucl. Med., 40(1), pp. 118-130, 1999.

C. Chen. L. Adler et al., "A non-linear spatially-variant object-dependent system model for prediction and correction of partial volume effect in PET", IEEE Trans. Med. Imag., 17: 214-227, Apr. 1998.

I. Weinberg et al., "Preliminary Results for Positron Emission Mammography: Real-Time Functional Breast Imaging in a Conventional Mammography Gantry", Eur. J. Nucl. Med., 23(7):804-806, Jul. 1996.

R. Miyaoka, "Dynamic high resolution positron emission imaging of rats", Biomed. Sci. Instrum. 1991, 27:35-42.

D. Townsend et al., "High Density Avalanche Chamber (HIDAC) Positron Camera", J. Nucl. Med., vol. 28, No. 10:1554-1562, 1987.

C. Thompson et al., "Feasibility Study for Positron Emission Mammography", Med. Phys. Apr. 1994, 21(4):529-538.

R. Ott, "The Applications of Positron Emission Tomography to Oncology", Br. J. Cancer, 1991, vol. 63, No. 3, pp. 343-345.

J. Tillisch et al., "Reversibility of caridiac wall motion abnormalities predicted by positron emission tomography", New Engl. J. Med., Apr. 3, 1986, vol. 314, No. 14: 884-888.

D. McCracken, "The Monte Carlo method", Sci. Am. 192, 90-96, May 1955.

D. Raeside, "Monte Carlo principles and applications", Phys. Med. Biol., vol. 21, No. 2, 181-197 (1976).

N. Keller and J. Lupton, "PET detector ring aperture function calculations using Monte Carlo techniques", IEEE Trans. Nucl. Sci. Feb. 1983, vol. NS-30, No. 1, pp. 676-680.

C. Thompson et al., "PETSIM: Monte Carlo simulation of all sensitivity and resolution parameters of cylindrical positron imaging systems", Phys. Med. Biol., 1992, vol. 37(3), pp. 731-749.

W. Moses et al., "Design of a High Resolution, High Sensitivity PET Camera for Human Brains and Small Animals", IEEE Transactions on Nuclear Science, vol. NS-44, No. 4, pp. 1487-1491, Aug. 1977.

I. Weinberg et al., "Biopsy-Ready PEM Scanner with Real-Time X-Ray Correlation Capability", accepted for presentation at IEEE Nucl. Sci. Symp. 2002.

I. Weinberg et al., "Implementing reconstruction with hand-held gamma cameras", Proceedings IEEE Nuc. Sci. Symp. 2000.

D.S. Lemons and B. J. Albright, "Quiet Monte-Carlo radiation transport", Journal of Quantitative Spectroscopy and Radiation Transfer, vol. 74, pp. 719-729 (2002).

F. Daghighian, et al., "Intraoperative beta probe: a device for detecting tissue labeled with positron or electron emitting isotopes during surgery", Med. Phys., vol. 21(1), pp. 153-157, Jan. 1994.

A. Chatziioannou et al., "Performance Evaluation of Micro-PET: A High-Resolution Lutetium Orthosolicate PET Scanner for Animal Imaging", J. Nucl. Med. 1999, 40:1164-1175.

\* cited by examiner

MISSION-SPECIFIC POSITRON EMISSION TOMOGRAPHY

CROSS REFERENCE TO RELATED APPLICATIONS

This application claims priority under 35 U.S.C. 119(e) to U.S. Provisional Application Ser. No. 60/402,535, entitled "Mission Specific PET", filed Aug. 12, 2002, the contents of which are incorporated by reference herein.

BACKGROUND OF THE INVENTION

1. Field of the Invention

The present invention relates to an apparatus and a method for detecting and delineating cancerous lesions, and more particularly an apparatus and a method for effective and affordable early detection of cancerous lesions using gamma rays or other radiation to obtain image data.

2. Description of the Related Art

As medical therapies become more biochemically specific, medical researchers and practitioners have turned to molecular imaging to develop new therapies and guide treatment with these therapies. Positron emission tomography ("PET") is the archetypal molecular imaging device, due to its high sensitivity to extremely small amounts of biochemically-relevant molecular probes. With such small amounts (e.g., tracer quantities), it is possible to monitor biochemical processes without substantially altering enzymatic kinetic rates.

The detection of early primary cancers with whole-body PET has been less successful than the detection of metastatic activity. This performance difference has been ascribed to instrumental limitations, as well as biological differences between primary cancers as compared to metastases. In general, it is preferable to detect primary cancers when they are small, since the chances of cure and control are substantially increased. The small size of early cancer reduces lesion detectability because of the finite resolution of the PET device, which effectively reduces lesion-to-background contrast. In the PET field, reduced lesion-to-background contrast can be quantitatively measured with the recovery coefficient. This effect has been extensively explored in phantom and clinical trials by Dr. Lee Adler. For example, see "Simultaneous Recovery of Size and Radioactivity Concentration of Small Spheroids with PET Data", C. Chen, L. Adler et al., J. Nucl. Med. 40(1), 1999, pp. 118–130; and "A Non-Linear Spatially Variant Object-Dependent System Model for Prediction and Correction of Partial Volume Effect in PET", C. Chen, L. Adler et al., IEEE Trans. Med. Imag. 17:214–227, 1998.

In U.S. patent application Ser. No. 09/737,119, Publication No. 20010040219, Cherry et al. disclose a detector for use in a dedicated PET scanner for cancer applications, particularly breast cancer applications, using at least two detector plates containing arrays of LSO or light-equivalent scintillating crystals and a fiber-optic bundle serving as a light-guide between the scintillator arrays and photomultiplier tubes. However, in the Cherry system, a fiber-optic bundle must be placed in at least two detector plates. In addition, in the Cherry system, the fiber-optic light guides are attached to the scintillator arrays and to the photomultipliers permanently, and these attachments are fixed and not removable. Such a fixed and non-removable arrangement may lead to practical difficulties when, for example, a medical intervention using data provided by the system requires physical access that may be obstructed by the fibers, or when the scintillator arrays and/or fiber optics are contaminated by body fluids so as to require disposal or sterilization. Thus, there is a need for a more flexible PET scanner system that allows the optical fibers to be removable from a photomultiplier or scintillator.

SUMMARY OF THE INVENTION

Advantageously, the invention provides a new algorithm for imaging reconstruction and simulation methods, including an application of Monte Carlo methods or deterministic sampling using Gaussian quadrature to constructing a transition matrix for purposes of iterative image reconstruction. The invention also provides the advantageous feature of an application of deterministic sampling using Gaussian quadrature to perform a transport calculation for purposes of simulating a medical imaging system which is sensitive to gamma-ray or other radiation emitted by the body.

In another aspect, the invention advantageously provides a handheld gamma camera or PET system with a disposable detector head, including a configuration of a gamma camera or PET scanner in which optical fibers or bundles of optical fibers are coupled to a scintillator or array of scintillators and the other end of the optical fibers or bundles of optical fibers are coupled to a light-sensitive camera (for example a photomultiplier). The invention may further include a mechanism to rapidly couple and/or decouple the optical fiber or fibers from the light sensitive camera or from the scintillator or array of scintillators so that the detector can be disposed of or sterilized without damaging the light-sensitive camera. The invention may further include a configuration in which a fiber-optic array couples one detector plate to a light-sensitive camera, while a second detector plate does not require a fiber-optic array.

In another aspect, the invention advantageously provides a free-hand scanner using the aforementioned new algorithm for imaging reconstruction and simulation to generate a transition matrix (which relates response of detector geometric properties to source geometry) which is used to reconstruct images.

DETAILED DESCRIPTION OF THE INVENTION

Reduced lesion detectability due to resolution limitations is a well-known phenomenon in the medical imaging arena. For example, the exacting requirements of breast cancer detection have led to construction of ultrahigh resolution x-ray devices, specifically designed for breast imaging. Naviscan PET Systems (formerly known as PEM Technologies) has set the standard for dedicated breast imaging using PET; for example, see U.S. Pat. No. 5,252,830. The first Naviscan PET Systems product was a breast-specific PET scanner with better than 3-mm full-width half maximum [FWHM] spatial resolution.

Just as in x-ray imaging, there are often good reasons to build mission-specific PET imaging devices. Building a whole-body PET scanner with 2-mm resolution, as would be required to reliably detect early cancers in the breast, would be very expensive. Whole-body PET scanners utilize hundreds of expensive photomultipliers which result in resolutions on the order of 6-mm FWHM. Improving spatial resolution by a factor of three, as would be needed to significantly reduce contrast recovery problems, would require replacing conventional photomultipliers by even more expensive models, substantially increasing construction costs. Although ingenious schemes have been developed that attempt to reduce construction costs of high resolution PET systems, these methods have yet to be applied to commercially available whole-body products, and would in any case be just as effective in reducing the cost of smaller dedicated mission-specific instruments. In a dedicated breast PET device, since the field of view is restricted to the breast, reaching even sub-millimeter resolution, as has been achieved by using of state-of-the-art technology, could potentially become affordable.

Aside from purely economic considerations, there are functions that are considered necessary for certain clinical missions that are difficult if not impossible to deliver with conventional whole-body PET scanners. These functions relate to cross-modality correlations (e.g., with ultrasound or x-ray mammography) and interventional/biopsy capability. Newly-introduced imaging devices that combine PET with x-ray computed tomography (i.e., PET/CT scanners) can be used to perform biopsy of lesions in stable organs (e.g., liver metastases), but would be difficult to use for mobile organs that are less amenable to CT-guided biopsy (e.g., ovary or bowel). With respect to interventional/biopsy capability, short scan times are highly desirable, and dedicated PET instruments can benefit from significantly increased collection efficiencies as compared to conventional ring scanners. In the case of dedicated breast PET, the combination of reduced attenuation losses (e.g., 5 cm of fatty breast tissue as compared to 50 cm of chest and breast) and increased solid angle coverage—due to reduced r-squared distance between the body part and the detector—can dramatically decrease scan time required to confidently visualize subtle lesions. It is noted that a lesion is defined as a local area in the body which may be harmful to the patient. For example, a lesion may be a cancer, an inflammatory process, or a necrotic area of tissue.

Not all clinical problems merit the development of mission-specific scanners. However, Naviscan PET Systems has identified several medical market niches in oncology that may justify the development and commercialization of such products: breast, prostate, ovary, and liver metastases. Outside of oncology, there are potential applications to cardiac surgery and treatment of infectious disease; for example, selection of appropriate borders for amputation in osteomyelitis, and selection of locations for endoscopic biopsy in tuberculosis. From a commercialization point of view, there are several examples of mission-specific products that have been highly valued in the marketplace once reimbursement patterns became well-defined. Examples include bone densitometry and spot digital mammography for breast biopsy.

From a public health point of view, the construction of cost-effective devices incorporating PET technology enables diffusion of molecular imaging into the broader medical community. This pattern is expected to improve delivery of health care to the public by allowing non-radiological specialists to deliver therapy on a more rational basis (e.g., on the basis of individual biochemistry profiles), consistent with current concepts in oncology which look at the individual's tumor type as only the first step in choosing tailored therapy.

Outside of oncology, PET has been shown to be effective in predicting myocardial viability. If a portable PET scanner is available for use in the cardiac surgery suite, it may be possible to immediately assess the adequacy of supply to reperfused myocardium. Portable PET scans can be used to guide bone removal in osteomyelitis, potentially reducing the degree of amputation required to effect a cure.

Monte Carlo methods may be used advantageously in conjunction with the present invention. Historically, simulation studies were first developed when experiments were prohibitive in cost, time, or other factors. Von Neumann coined the phrase Monte Carlo when he applied random sampling to calculate neutron diffusion rates during the Manhattan Project. Monte Carlo simulations are based on the construction of a stochastic model in which the expectation value of a random variable is equivalent to the measured physical quantity. This expectation value is estimated by the average of multiple independent samples representing this random variable, obtained by random sampling. For example, consider a random variable X which is needed for a problem involving photon propagation in tissue. This variable might be the angle of deflection a scattered photon may experience due to a scattering event. Associated with this random variable is a probability density function over a given interval. The integral of this probability density function is normalized to unity over this interval, which corresponds to the fact that any sampling of the random variable must lie in the given interval. To model a more complex system, the outcomes of each random sampling are accumulated under appropriate weights and any rejection algorithms to arrive at an expected value of a given measurable physical quantity.

Monte Carlo techniques were introduced into medical physics by Raeside in 1976 and to PET by Keller in 1983. Full PET devices have been simulated using GEANT, a code developed by high energy physicists that included the ability to specify detector geometry, and with adaptations of older codes developed by Keller and Lupton. These simulations have modeled classic ring geometries for PET devices for both human and animal varieties. Works-in-progress presentations have been made about parallel-plate and square detector rings.

Preliminary results have been obtained by the present inventors demonstrating proof-of-principle for an endoscopic PET scanner and for a novel application of code to replace traditional Monte Carlo calculations. Naviscan PET Systems has used Monte Carlo methods extensively in conducting simulations of both fixed and free-hand geometries. For example, Monte Carlo methods have been used to create transition matrices for reconstruction. Specifically, these methods relate to the reconstruction that is required to provide a high quality image of an unknown distribution of radioactive sources. Reconstruction is often performed with an iterative technique, in which a computer compares the calculated response of the imaging system to successive guesses as to the distribution with the actual measured response as measured by the imaging system. In order to calculate the response of the imaging system to these guesses, a "transition matrix" is used to model the imaging system. In most imaging devices, this transition matrix is generated by examining a fixed detector geometry and a fixed volume in which the unknown radioactive source distribution is allowed to occupy. In accordance with an embodiment of the invention, for more flexible imaging systems, the position of a freed detector head is determined, and the transition matrix is calculated using Monte Carlo or deterministic sampling methods. In accordance with another embodiment of the invention, Monte Carlo and/or deterministic sampling methods may be used for modeling systems with the aim of improving design.

It is known that a transition matrix that models the response of the detection system to arbitrary distributions of radioactivity is needed in order to assist a PET system in performing image formation (e.g., through iterative image reconstruction). Other types of reconstructions, such as filtered backprojections, may also employ transition matrices to form an image. According to a preferred embodiment of the present invention, the use of Monte Carlo and/or deterministic sampling methods allow the PET system to have great flexibility, because the trajectory of the fiber-optic mounted scintillator can be tracked by a position sensor. This trajectory can be inputted into the Monte Carlo and/or deterministic sampling algorithm to create a transition matrix for a PET or gamma ray imaging system incorporating the tracked fiber-optic mounted scintillator array. The imaging system may include other components, possibly using timing coincidence (also referred to as coincidence gating, or coincident gating). Specifically, the other components may include a detector plate mounted outside the body. Additionally, tracking of the fiber-optic mounted scintillator array may be accomplished with a method other than a position sensor, for example, by using a position encoder such as a moveable lever that can place the scintillator array in a known set of positions.

Figure 8:
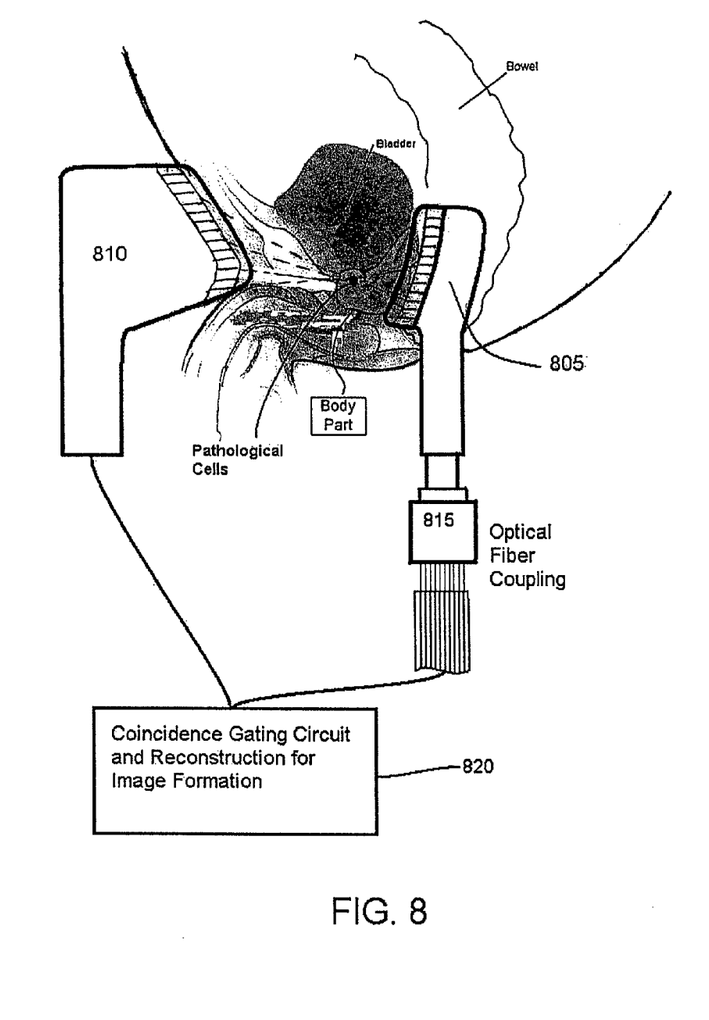
FIG. 8 shows a schematic drawing of a prostate imaging device having biopsy and ultrasound compatibility, according to a preferred embodiment of the invention.

Coincidence gating is the method of aggregating events depending on the period of time between detection of these events by the imaging system. Referring to FIG. 8, coincidence gating 820 can be applied in electronic form (e.g., with AND circuitry that only allows pulses within a specific time interval to generate a gate signal), or post-acquisition by examination of list files showing when each event was detected by the imaging system. Other forms of coincidence gating or detection may be used as well.

Figure 1:
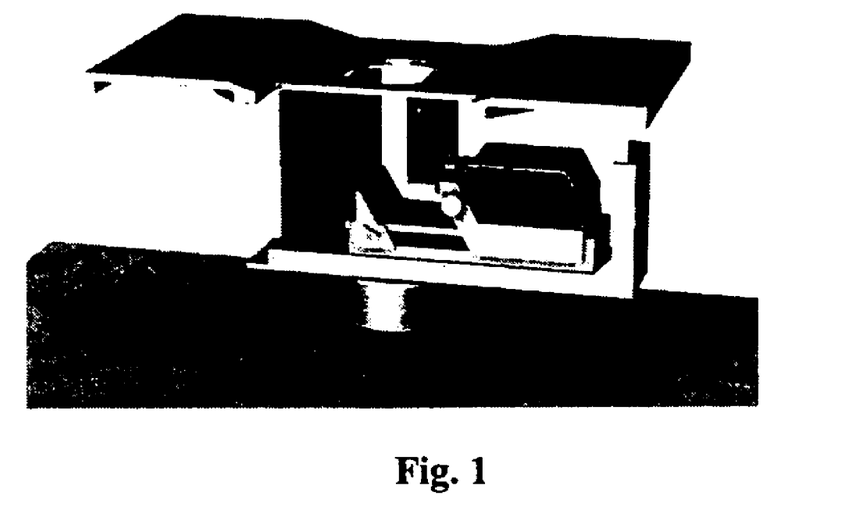
FIG. 1 shows a diagram of a PEM-2400 dedicated breast camera mounted in a stereotactic x-ray mammography unit.
Figure 2:
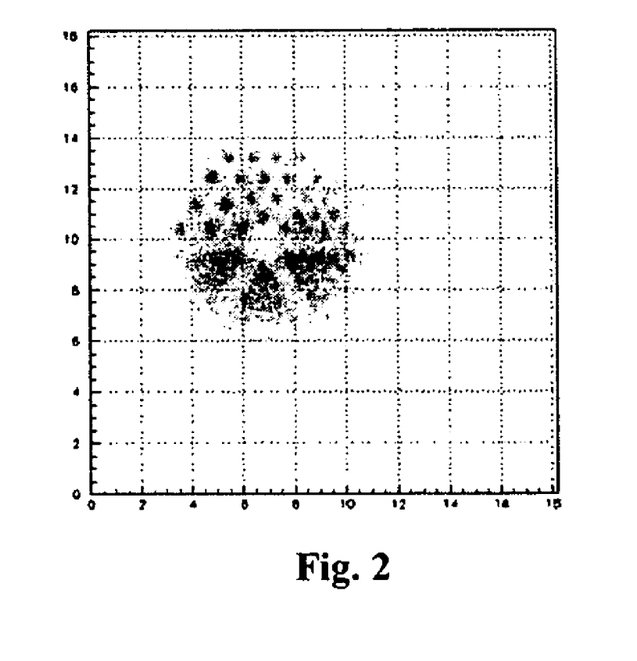
FIG. 2 shows a hot spot phantom diagram that illustrates clear visualization of 1.5 mm hot spots.

As is traditional for light guide fabricators, dedicated breast imaging PET designs were performed with the assistance of Monte Carlo models, which enabled clear identification of 2-mm crystal pitches with very low profile light guides. These low-profile light guides enabled the building of PET detector heads for mammography that were very compact (e.g., less than 6 cm deep). Referring to FIG. 1, a diagram of a PEM-2400 breast camera mounted in a Lorad stereotactic x-ray mammography unit is shown. These detector heads are so small that they can stay mounted in a stereotactic mammography camera without requiring removal of the x-ray detector. Referring to FIG. 2, an exemplary hot spot phantom diagram that illustrates clear visualization of 1.5 mm hot spots can be obtained from a camera such as that illustrated in FIG. 1.

Figure 3:
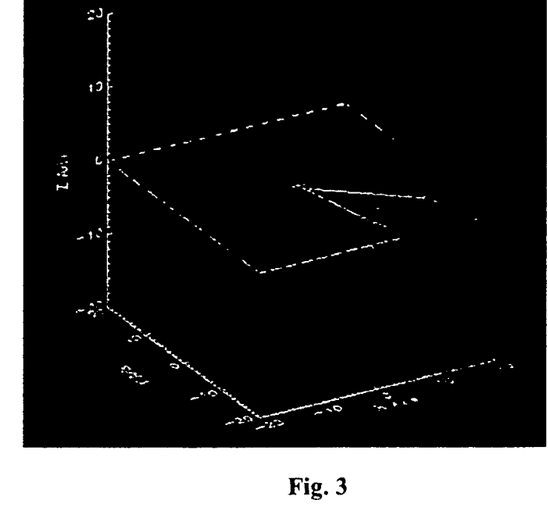
FIG. 3 shows a graph of an exemplary position of detector heads from a hand-held PET scanner.
Figure 4:
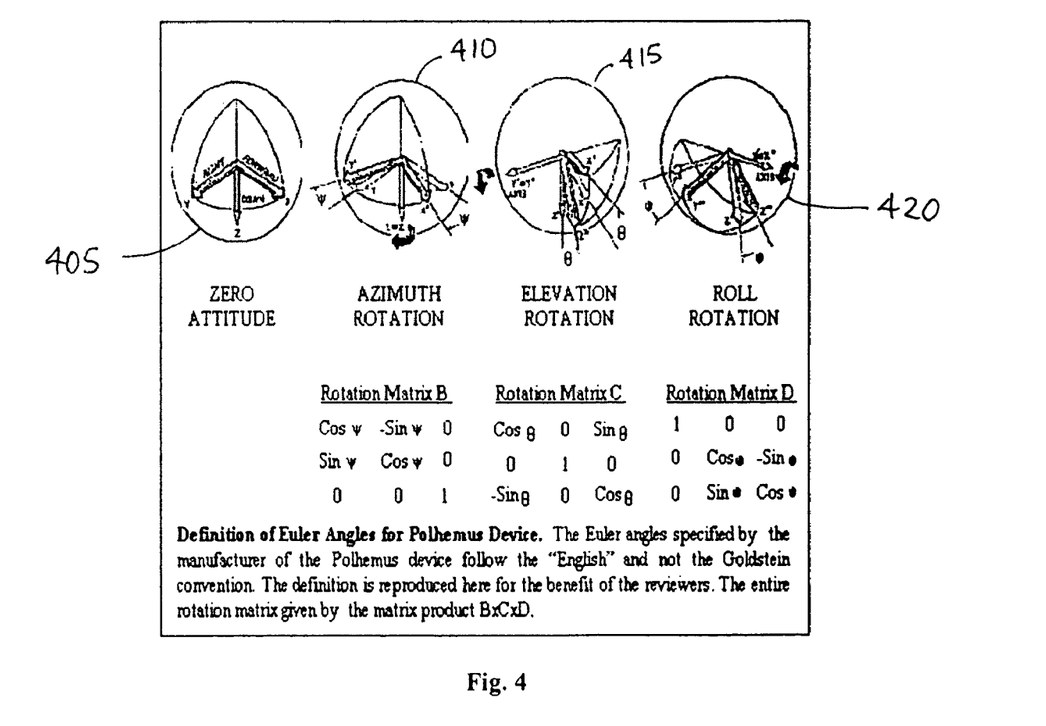
FIG. 4 illustrates an exemplary diagram of a graphical user interface that shows hand-held PET scanner detector heads as rigid bodies, with lines of response generated by a source between the detector heads.

Referring to FIGS. 3 and 4, for free-hand geometries, it is possible to collect the information about the orbits experienced by a hand-held scanner and project all possible line-pairs from a source volume that could be intercepted by the scanner traversing the orbit. In FIG. 3, an exemplary position of detector heads from a hand-held PET scanner is shown. FIG. 4 illustrates an exemplary diagram of a graphical user interface that shows hand-held PET scanner detector heads as rigid bodies, with lines of response generated by a source between the detector heads, including lines of response for zero attitude 405, azimuth rotation 410, elevation rotation 415, and roll rotation 420. The present inventors have extended this principle to allow the orbit itself to be specified through a random walk, in order to compare various detector geometries. Prototype free-hand SPECT and PET devices have been built, which are able to image point sources and remove overlapping activity by using Monte Carlo based reconstructions.

For a stochastic orbit, the field-of-view of the system is constrained mathematically within a specified detection volume in which the detectors can be located.

Naviscan PET Systems has pioneered adoption of a new computational method that promises to significantly reduce computational time for simulations. This method incorporates deterministic sampling using Gaussian quadrature, and has been shown to speed up transport codes in plasma physics by a factor of one thousand. The code is fast, efficient, rapidly convergent, and highly parallelizable. It is based on a technique of replacing each call to a random number generator with a carefully chosen and deterministic realization of the random variable. In other words, in place of calling a random number generator, the weights and abscissas of the relevant Gaussian quadrature parameters are used. For example, in many imaging algorithms, a Monte Carlo calculation requires a random realization of the random variable $N(0,1)$ (i.e., a random variable of mean zero and variance unity) defined by a Gaussian probability density function $p(x)=\exp(-x^2/2)$. In the case of $p(x)$, the relevant Gaussian quadrature parameters are simply the well-known Gauss-Hermite weights $w_j$ and abscissas $q_j$. For example, instead of making two Monte Carlo random samplings, two deterministic samplings are obtained from the n=2 Gauss-Hermite abscissa-weight pairs. For n=2, these pairs are simply $q_j=(-0.57735, +0.57735)$ and $w_j=(1, 1)$.

This method is based on exploiting a theorem from Gaussian integration that states that for a function $f(x)$, the following approximation:

$$\int_{-\infty}^{\infty} f(x) \exp(-x^2/2)\, dx \approx \sqrt{2\pi} \sum_{j=1}^{J} w_j f(q_j)$$

becomes exact if the weights $w_j$ and abscissas $q_j$ are Gauss-Hermite and the function $f(x)$ is a linear combination of the 2J−1 polynomials $x^0, x^1, \ldots, x^{2J-1}$.

Figure 5:
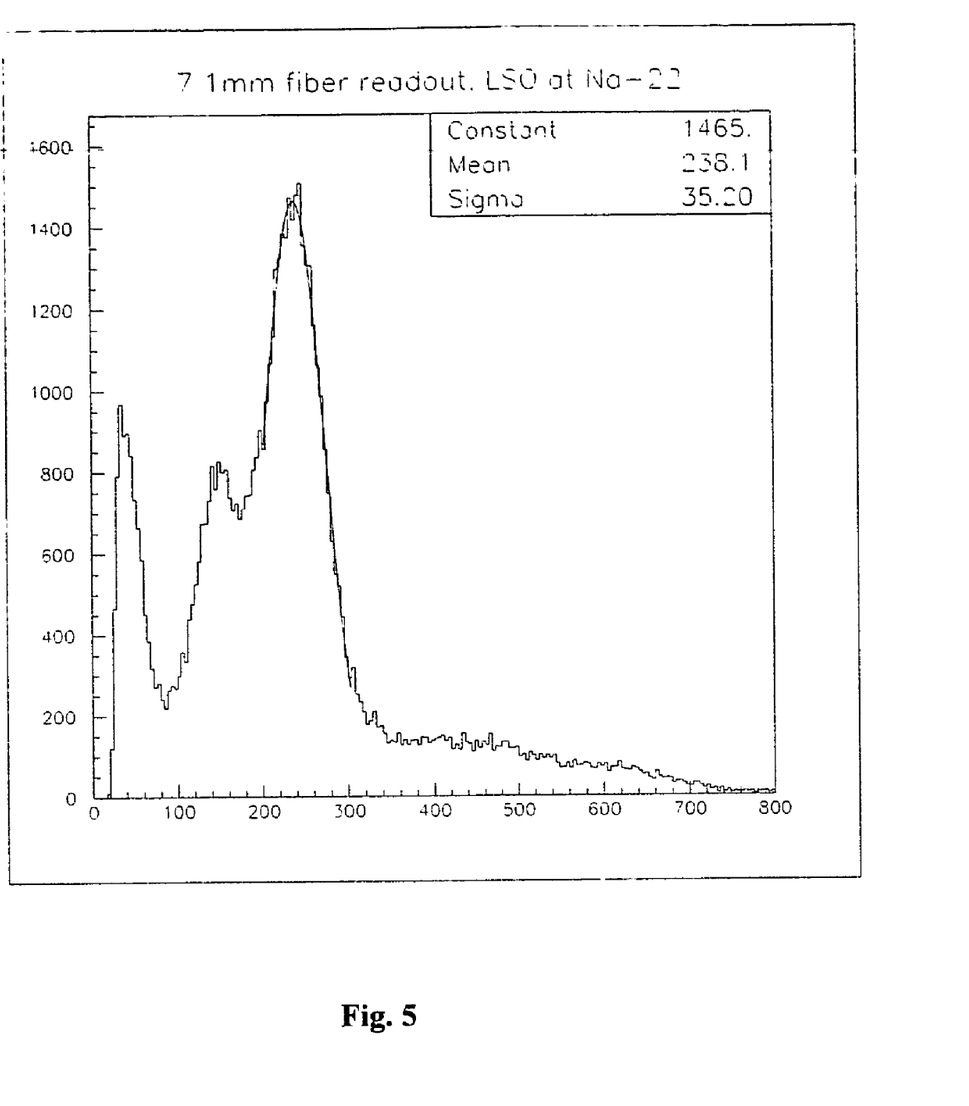
FIG. 5 shows an exemplary graph of an energy spectrum of a crystal in a compact array for endoscopy.

In addition to compact light guides for breast imaging, the present inventors have developed compact cameras for endoscopy that fit on fiber optic bundles according to a preferred embodiment of the invention. Referring to FIG. 5, an exemplary energy spectrum for one of 24 crystals in an array is shown. In example shown in FIG. 5, the crystal that produced the energy spectrum is approximately 2 mm thick, and the compact array has a diameter of approximately 1 cm.

Figure 6:
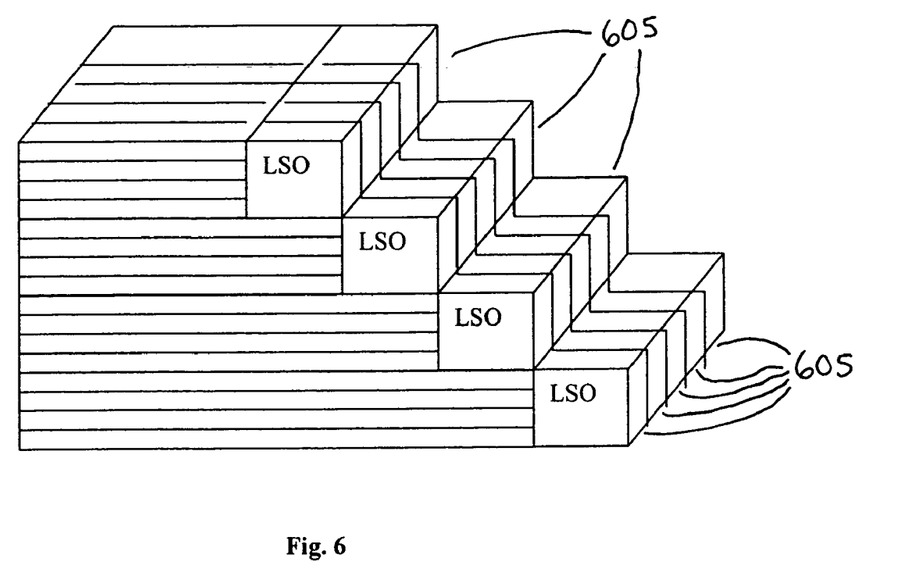
FIG. 6 shows a side view of a detector array according to a preferred embodiment of the invention. The detector array comprises scintillating crystals, each of which is attached to a fiber-optic tail. The fiber-optic tails which are arranged in a bundle.
Figure 7:
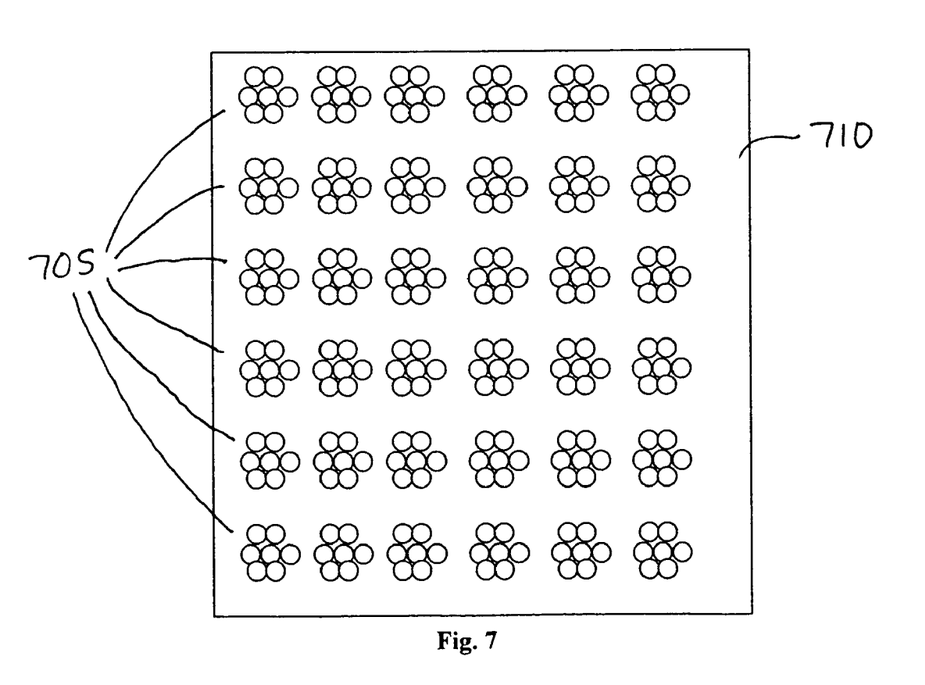
FIG. 7 shows a diagram of the fiber optics as they separate from the bundle and are attached to a position-sensitive photomultiplier face, as constructed according to a preferred embodiment of the invention.

Referring to FIG. 6, an exemplary array design for a detector head of the endoscopy camera is shown. In this example, the detector head includes a total of 32 lutetium oxyorthosilicate ("LSO") crystals 605, arranged in an 8×4 array. Each LSO crystal 605 is 2 mm×4 mm×5 mm. Thus, in this example, the total volume required by the detector head is approximately 1.3 cm$^3$. A conventional small field-of-view array volume is about 43 cm$^3$, which is about 33 times as large as that depicted in FIG. 6. Thus, the detector shown in FIG. 6 represents an improved pixel resolution of a factor of 33. For example, if a conventional detector yields a count rate of 1 kHz, then the detector of FIG. 6 will yield a count rate of about 30 Hz, which is equivalent to about 1 true Hz per pixel. In addition, each LSO crystal 605 couples with seven optical fibers, and, referring also to FIG. 8, the coupling 815 between the crystal 605, or array of crystals 605 contained within component 805, and the fibers is designed so that the fibers can be easily decoupled from the crystal. In other words, although the fibers are actually physically attached to the crystal, the fibers are removable and disposable, for situations in which, for example, a medical intervention requires access that would otherwise be obstructed by the fibers. The quality of removability of the fibers may be implemented by fiber-optic couplers and ferrules, or by other conventional methods of coupling fiber-optic bundles to imaging devices or to other fiber-optic bundles. Referring to FIG. 7, a cross-sectional view of a six-by-six array is also shown, including several fiber optic bundles 705 on the face 710 of the camera. Each of the fiber optic bundles 705 includes seven fibers, each of which is approximately 1 mm in diameter.

Referring to FIG. 8, the present invention further provides a design for a prototype endoscopic PET camera. This camera has two components, including an ultra-compact endoscopic component 805 in coincidence with a larger external component 810, similar to a device for prostate imaging as disclosed in U.S. patent application Ser. No. 10/196,560. The device includes two components: (1) an ultra-compact intracavitary component 805 comprising a small (e.g., 1 cm diameter) array of thin (e.g., 2 mm by 5 mm) LSO crystals mounted on fiber optics that are attached to a position-sensitive photomultiplier, and (2) an external component array 810 of detectors and photomultipliers placed anterior or posterior to the patient. In principle, placing detectors on the ends of fibers has been done before (e.g., for animal scanners), although the motivation in those cases was to allow deployment of large photomultipliers in observing a small volume. Gamma detectors have also been placed on the ends of fiber optics in order to build non-imaging gamma probes. The present inventors have extended these concepts to better suit the needs of endoscopists, by making several enabling modifications, including the following: 1) introducing a quick-release optical fiber coupling so that the detector head is separable from the photomultiplier, and is therefore disposable; 2) adding position sensing to the detector head so that events can be correctly placed in sinograms; 3) including flexible Monte Carlo-based reconstruction algorithms to allow reconstruction of events from the mobile detector head and a second detector head placed external to the body; and 4) using deterministic sampling to accelerate these reconstruction algorithms. These advantageous features allow the present invention to be useful to surgeons and endoscopists, who can kill or remove cancer or inflammatory cells and then use the present invention to check to ensure that the cells are actually removed or dying. Then, the present invention can be further utilized to check the field of surgery (or other therapy) to determine whether residual viable cells are present, proceeding iteratively to minimize the number of residual viable cells.

While the present invention has been described with respect to what is presently considered to be the preferred embodiment, it is to be understood that the invention is not limited to the disclosed embodiments. To the contrary, the invention is intended to cover various modifications and equivalent arrangements included within the spirit and scope of the appended claims. For example, the above descriptions of embodiments of the invention are primarily couched in terms of using a PET scanner system. Those skilled in the art will understand that a compact gamma camera system using coincidence gating (i.e., a coincident gamma camera system) may also be used. The scope of the following claims is to be accorded the broadest interpretation so as to encompass all such modifications and equivalent structures and functions.

The contents of each of the following publications are hereby incorporated by reference:

1) S. Holbrook, "Newsline Commentary", Journal of Nuclear Medicine 43(2), p. 12N, 2002.
2) L. P. Adler et al., "Evaluation of Breast Masses and Axillary Lymph Nodes with [F-18] 2-Deoxy-2-fluoro-D-glucose PET", Radiology, 1993, 187: 743–750.
3) B. Fisher et al., "Cancer of the Breast: Size of Neoplasm and Diagnosis", Cancer, 1969, 24:1071–1080.
4) R. M. Kessler et al., "Analysis of emission tomographic scan data: limitations imposed by resolution and background", J. Comput. Assist Tomography, 1984, 8:514–522.
5) C. Chen, L. Adler et al., "Simultaneous Recovery of Size and Radioactivity Concentration of Small Spheroids with PET Data", J. Nucl. Med., 40(1), pp. 118–130, 1999.
6) C. Chen. L. Adler et al., "A non-linear spatially-variant object-dependent system model for prediction and correction of partial volume effect in PET", IEEE Trans. Med. Imag., 17: 214–227, 1998.
7) U.S. Pat. No. 5,252,830.
8) I. Weinberg et al., "Preliminary Results for Positron Emission Mammography: Real-Time Functional Breast Imaging in a Conventional Mammography Gantry", Eur. J. Nucl. Med., 23(7):804–806, 1996.
9) R. Miyaoka, "Dynamic high resolution positron emission imaging of rats", Biomed. Sci. Instrum. 1991, 27:35–42.
10) D. Townsend et al., "High Density Avalanche Chamber (HIDAC) Positron Camera", J. Nucl. Med., 28:1554–1562, 1987.
11) C. Thompson et al., "Feasibility Study for Positron Emission Mammography", Med. Phys. 1994, 21:529–538.
12) R. Ott, "The Applications of Positron Emission Tomography to Oncology", Br. J. Cancer, 1991, 63:343–345.
13) J. Tillisch et al., "Reversibility of cardiac wall motion abnormalities predicted by positron emission tomography", New Engl. J. Med. 314: 884–8, 1986.
14) D. McCracken, "The Monte Carlo method", Sci. Am. 192, 90–96 (1955).
15) D. Raeside, "Monte Carlo principles and applications", Phys. Med. Biol. 21, 181–197 (1976).
16) N. Keller and J. Lupton, "PET detector ring aperture function calculations using Monte Carlo techniques", IEEE Trans. Nucl. Sci. 30, pp. 676–680 (1983).
17) C. Thompson et al., "PETSIM: Monte Carlo simulation of all sensitivity and resolution parameters of cylindrical positron imaging systems", Phys. Med. Biol., 1992, Vol. 37(3), pp. 731–749.
18) W. Moses et al., "Design of a High Resolution, High Sensitivity PET Camera for Human Brains and Small Animals", IEEE Transactions on Nuclear Science NS-44, pp. 1487–1491, 1977.
19) W. Worstell et al., "Monte Carlo-based Implementation of the ML-EM Algorithm for 3-D PT Reconstruction", Proceedings IEEE Nucl. Sci. Symp. 1997.
20) I. Weinberg et al., "Crystal Identification in Modular 2-Dimensional Array Detectors for High Spatial Resolution PET", Proc. Intl. Wksp. on Physics and Engineering in Computerized Multi-dimensional Imaging and Processing, SPIE V.
21) I. Weinberg et al., "Biopsy-Ready PEM Scanner with Real-Time X-Ray Correlation Capability", accepted for presentation at IEEE Nucl. Sci. Symp. 2002.
22) I. Weinberg et al., "Implementing reconstruction with hand-held gamma cameras", Proceedings IEEE Nuc. Sci. Symp. 2000.
23) D. S. Lemons and B. J. Albright, "Quiet Monte-Carlo radiation transport", Journal of Quantitative Spectroscopy and Radiation Transfer, Vol. 74, pp. 719–729 (2002).
24) U.S. patent application Ser. No. 10/196,560, filed Jul. 17, 2002.
25) A. Chatziioannou et al., "Performance Evaluation of Micro-PET: A High-Resolution Lutetium Orthosolicate PET Scanner for Animal Imaging", J. Nucl. Med. 1999, 40:1164–1175.
26) F. Daghighian, et al., "Intraoperative beta probe: a device for detecting tissue labeled with positron or electron emitting isotopes during surgery", Med. Phys., Vol. 21(1), pp. 153–157, January 1994.
27) U.S. application Ser. No. 09/737,119, Publication No. 20010040219, filed Dec. 14, 2000.
28) U.S. application Ser. No. 09/833,110, filed Apr. 11, 2001.
29) U.S. Pat. No. 6,331,703.
30) U.S. patent application Ser. No. 10/027,759, filed Dec. 21, 2001.

What is claimed is:

1. A method of reconstructing image data to select borders for removal or killing of pathological cells within a body part using a positron emission tomography (PET) scanning system having at least a first detector head and a second detector head, the first and second detector heads being sensitive to radiation emitted by the body part, and the method comprising the steps of:
a) positioning the first detector head within a body cavity;
b) positioning the second detector head external to the body part;
c) using coincidence gating to record data obtained by the first and second detector heads from the radiation emitted by the body part;
d) applying Monte Carlo methodology to assist in an image reconstruction or in an image formation using the recorded data;
e) using the reconstructed or formed image to detect pathological cells;
f) removing tissue from the body part based on the reconstructed or formed image; and
g) iterating steps a, b, c, d, e, and f to minimize an amount of residual viable pathological cells in the body part.

2. The method of claim 1, wherein the first detector head is coupled to a plurality of optical light fibers, and wherein the plurality of optical light fibers are configured to be detachable from the first detector head.

3. A method of reconstructing image data to select borders for removal or killing of pathological cells within a body part using a positron emission tomography (PET) scanning system having at least a first detector head and a second detector head, the first and second detector heads being sensitive to radiation emitted by the body part, and the method comprising the steps of:
a) positioning the first detector head within a body cavity;
b) positioning the second detector head external to the body part;
c) using coincidence gating to record data obtained by the first and second detector heads from the radiation emitted by the body part;
d) applying deterministic sampling using Gaussian quadrature parameters to assist in an image reconstruction or in an image formation using the recorded data;
e) using the reconstructed or formed image to detect pathological cells;
f) removing tissue from the body part based on the reconstructed or formed image; and
g) iterating steps a, b, c, d, e, and f to minimize an amount of residual viable pathological cells in the body part.

4. The method of claim 3, wherein the first detector head is coupled to a plurality of optical light fibers, and wherein the plurality of optical light fibers are configured to be detachable from the first detector head.

* * * * *